United States Patent [19]

Joyce

[11] Patent Number: 4,604,016
[45] Date of Patent: Aug. 5, 1986

[54] MULTI-DIMENSIONAL FORCE-TORQUE HAND CONTROLLER HAVING FORCE FEEDBACK

[76] Inventor: Stephen A. Joyce, 1163 W. Eddy, Chicago, Ill. 60657

[21] Appl. No.: 520,056

[22] Filed: Aug. 3, 1983

[51] Int. Cl.$^4$ .............................................. B25J 3/00
[52] U.S. Cl. .......................................... 414/7; 414/5; 74/471 XY; 74/501 M
[58] Field of Search .................... 414/5, 6, 7; 244/234, 244/236, 237; 74/501 M, 471 XY; 128/1 R; 318/628; 364/190

[56] References Cited

U.S. PATENT DOCUMENTS

| | | | |
|---|---|---|---|
| 3,133,649 | 5/1964 | Serrell | 414/5 |
| 3,139,990 | 7/1964 | Jelatis et al. | 414/5 |
| 3,263,824 | 8/1966 | Jones et al. | 414/5 |
| 3,447,766 | 6/1969 | Palfreyman | 244/83 |
| 4,021,715 | 5/1977 | Hacht et al. | 318/628 |
| 4,150,803 | 4/1979 | Fernandez | 244/236 X |
| 4,216,467 | 8/1980 | Colston | 414/5 X |
| 4,221,516 | 9/1980 | Haaker et al. | 414/5 |
| 4,302,138 | 11/1981 | Zarudiansky | 414/5 |
| 4,459,870 | 7/1984 | Gill et al. | 74/471 XY |

FOREIGN PATENT DOCUMENTS 464659  1/1914  France ............................. 244/237

Primary Examiner—Donald W. Underwood
Attorney, Agent, or Firm—McDougall, Hersh & Scott

[57] ABSTRACT

A hand controller or 'cursor' for the actuation of slaved apparatus. The cursor includes a handle extending from a line attachment member comprised of four equally spaced legs. The ends of these legs define vertices of a regular tetrahedron. The cursor is supported within a subtending structure by a plurality of tension lines which may be connected to torque motors or to another controlled device. A control computer preferably interfaces the present controller with the slaved apparatus wherein signals representative of the several tension line lengths are translated by the computer into control signals actuating the slaved device. In addition, force transducers on the slaved mechanism generate signals representative of the forces encountered by the slaved device which, in turn, are translated by the computer into torque motor control signals thereby providing interactive cursor force-feedback.

10 Claims, 7 Drawing Figures

MULTI-DIMENSIONAL FORCE-TORQUE HAND CONTROLLER HAVING FORCE FEEDBACK

This invention relates to a hand controller or 'cursor' for the control and actuation of a wide variety of apparatus ranging from large mechanisms requiring relatively large forces to effect movement, at one extreme, to high precision devices requiring extremely fine motional control on the other end of the control spectrum. More specifically, the present invention relates to a multi-dimensional cursor suitable for control of apparatus along the three linear orthogonal axes as well as about three orthogonal torsional axes. The present invention further relates to an interactive force-feedback cursor permitting the user to "feel" the actual forces encountered by a slaved apparatus in response to manipulation of the control cursor.

The present controller is particularly suited for remote control of objects in hostile or otherwise inaccessible environments. Examples include airless environments such as the ocean floor or outerspace and radioactive environments such as the interior of a nuclear power station containment chamber.

In addition, certain environments are relatively inaccessible simply due to the travel times required to reach these remote locations. A highly skilled surgeon possessing, for instance, a certain specialized and unique capability could perform an emergency life-saving procedure utilizing the present controller where there is insufficient time to travel to the actual remote site of the operation. In essence, the surgeon may be, effectively, in several locations at once. Other locations are simply inaccessible irrespective of the time available to get there.

Yet another significant application for the present controller is force and/or motion amplification/attenuation in which either the size or weight of the object or "work piece" on which the controller is to operate requires that the range of movement or forces applied to the cursor (master) be scaled appropriately for application to the slaved mechanism.

The surgical procedure previously considered illustrates an application of the present controller wherein both the force and distance may advantageously be scaled. The extremely light forces and fine movements required for a microsurgical operation on a human nerve tissue, for example, may be scaled so that relatively greater forces and movements must be applied to the cursor by the surgeon. This permits the surgeon to make relatively gross hand motions with correspondingly increased cursor actuation forces without injury to the patient. In this manner, the surgeon can obtain a meaningful "feel" or touch for the work being performed where otherwise the extremely fine and precise nature of the procedure would fall below the threshold of human sensation thereby rendering "touch" sensory feedback impossible. Furthermore, this increased sensory "feel" obtainable with force/distance scaling lessens the likelihood of mistake or injury occasioned by the inadvertent application of excessive forces. Such down-scaling also finds application in the manufacturing or assembly of precision apparatus comprised of small or microscopic sized components.

At the other end of the spectrum, the scaling permitted by the present invention can be utilized where the workpieces are relatively heavy or where these objects must be moved over substantial distances. Applications for such force/distance up-scaling may be found in most heavy industrial environments, for instance, in a foundry or automobile assembly plant.

Yet another application for the present controller is the purely 'imaginary' or 'synthetic' environments generally created by computer. In a computer aided design facility, for example, it is often less expensive, and faster, to 'sculpt' or create the proposed new article utilizing computer graphics prior to committing to actual fabrication of a tangible model. In this way, it is possible to view and review alternative approaches at low cost before commencing actual model fabrication. Thus, the present force-feedback controller permits a designer to literally sculpt his model, with all the attendent visual and motor feedback sensations, as if the object were actually being modeled in clay or other material.

The present invention, however, is not limited to interactions with things which can actually be built. Purely imaginary constructions or 'untouchable', but real, objects may also be probed utilizing the present force-feedback cursor. One such example is the probing or manipulation of atoms, molecules, or other atomic particles. While such particles exist, in fact, it is not possible to physically 'touch' these particles and, therefore, probing must be accomplished with the present controller through computer simulation.

Known prior art controllers suffer from one or more deficiencies which render them unsatisfactory for precise multi-axes force-feedback hand control. Traditional 'joystick' type controllers, for example U.S. Pat. No. 3,447,766 to Palfreyman, provide only a restricted degree of control generally in two linear or torsional axes. Such limited motional control is wholly unsatisfactory for precision interactive control wherein six degrees of freedom of motion are required to permit full movement of the slaved apparatus. One known controller, U.S. Pat. No. 4,216,467 to Colston, does provide a six axis output but does not permit actual movement of the cursor; rather, the output signals are generated in response to the pressures applied to the otherwise inert controller actuator handle or cursor. In this regard, the Colston structure is unsatisfactory for use in the interactive force-feedback environment for which the present invention was specifically designed. In addition, the Colston controller employs combined tension/compression members which, as discussed below, have certain control system disadvantages.

Another deficiency of known controller structures relates to the force-feedback requirement and, specifically, to the complexity of the control systems necessary to eliminate closed-loop instabilities commonly associated with interactive controllers utilizing tension/compression force translating members. Mechanical linkages which are alternately operated in the compressive and tension modes or servo or torque motors which deliver both positive and negative output forces often exhibit undesirable 'back-lash' or other discontinuities, non-linearities, or regions of non-monotonicity that can result in unpredictable and unstable system operation unless properly compensated by the controller circuitry. This is due to the necessity that there be a continuous and smooth transition between the regions of compressive and tensioned operation of the interconnecting linkages and, similarly, that there exist a continous and smooth transition between the positive and negative force outputs of any servo or torque motor in the system.

Mechanical and electro-mechanical apparatus having the requisite continuity of operation are quite expensive and, in some instances, simply unavailable. Although sophisticated control circuitry may be employed to overcome these inherent mechanical limitations; little expense is avoided using this approach due to the cost of the control circuitry necessary to correct these inherent deficiencies. While the specific characteristics of each of the following prior art structures is not known in detail, it is believed that each such structure would exhibit undesirable mechanical back-lash requiring expensive control circuitry for use as a precison workpiece controller; Haaker, U.S. Pat. No. 4,221,516; Von Hacht, U.S. Pat. No. 4,021,715; Jelatis, U.S. Pat. No. 3,139,990; and Serrel, U.S. Pat. No. 3,133,649 response to the pressures applied to the otherwise inert controller actuator handle or cursor.

The controller of the present invention, by contrast, utilizes an arrangement of twelve tension-only lines interconnecting the cursor and the torque motors, or another controlled device, to effect full interactive force-feedback control in all three linear and three torsional axes. In this manner, the above described transition region effects are eliminated by maintaining a positive tensile force on each line with its corresponding unidirectional force from each respective torque motor. More specifically, the present controller employs a four vertex terahedral cursor arrangement suspended within a polyhedral (octahedral) supporting structure to properly position and interconnect the cursor with the twelve tension lines and thereby affording a high degree of user access to, and movement of, the cursor.

It is therefore an object of the present invention to provide an interactive force-feedback cursor and controller structure. The cursor shall have six independent degrees of movement including three linear axes and three torsional axes. Further, the cursor shall be suspended by an arrangement of twelve lines that shall continuously be under tension. A furher object of the present controller is the application of specific tensions on each control line in response to the movement of the cursor and the corresponding travel of the slaved apparatus thereby providing force-feedback to the user representative of the actual or simulated environment encountered by such controlled device. Another object is to provide a torque motor on each line whereby the tension on each line may be precisely controlled by a computer or other motor control apparatus. Further, it is an object of the present invention to provide means for measuring the length of each of the twelve lines whereby the precise location and orientation of the cursor may be determined, for example, by a controller computer. It is further contemplated that piezo-electric transducers, or the like, may be provided at the slaved apparatus whereby signals representative of the forces actually encountered by such slaved apparatus are provided for the force-feedback control of the cursor or cursor torque motors.

DESCRIPTION OF THE PREFERRED EMBODIMENT

Figure 1:
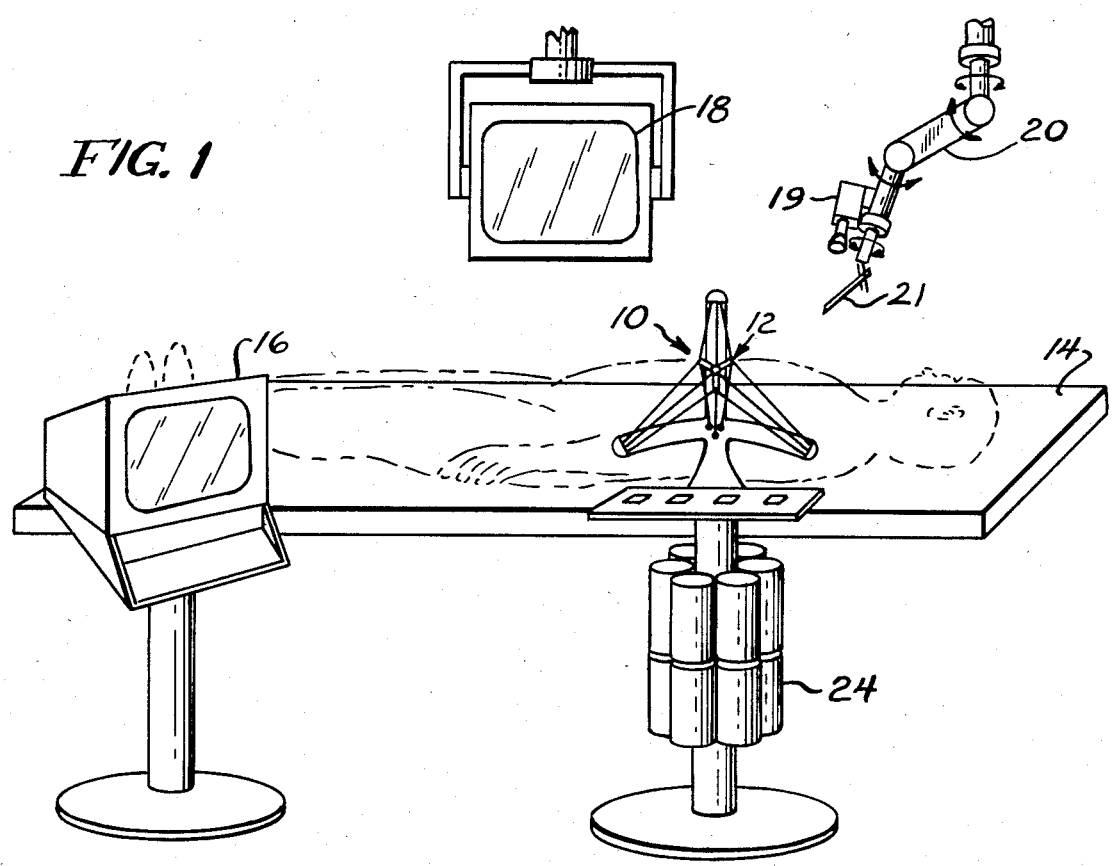
FIG. 1 illustrates the controller of the present invention including a control computer, monitor, interconnected with a slaved microsurgical engine.

FIG. 1 represents a typical installation of the force-feedback controller of the present invention as configured to perform microsurgical procedures. The illustrated work station includes a control actuator unit 10, having a cursor 12 positioned generally in the center thereof, a console or table 14 on which the controller is affixed, a computer terminal 16 with CRT display, a video monitor 18 and a camera 19, and a microsurgical operating engine 20 having a knife or other slaved tool 21. Camera 19 is preferably affixed to the surgical engine adjacent knife 21 to afford a clear video picture of the patient or other 'work-piece'. Cursor 12 is operatively interconnected through twelve tension lines 22 to cursor torque motors 24 positioned immediately below controller 10 and table 14.

In operation, the surgeon sits at the workstation console 14 with an unobstructed view of monitor 18 and manipulates cursor 12. The changing lengths of lines 22 are recorded by computer 16 and translated into corresponding movements of the microsurgical engine 20. Depending upon the particular procedure being performed, the force and distance outputs of the cursor may be scaled down by the computer prior to outputting to the surgical engine. The video camera 19 permits the surgeon to visually observe the results of his operative activities on monitor 18 while, importantly, the forces actually encountered by the microsurgical slaved "tools" are translated by computer 16 to torque motors 24 thereby providing a real-time interactive force-feedback response enabling the surgeon to 'feel' the operation in a manner similar to conventional operating procedures. Torque motors 24 additionally comprise conventional shaft encoders for measuring line lengths.

Figures 2, 3:
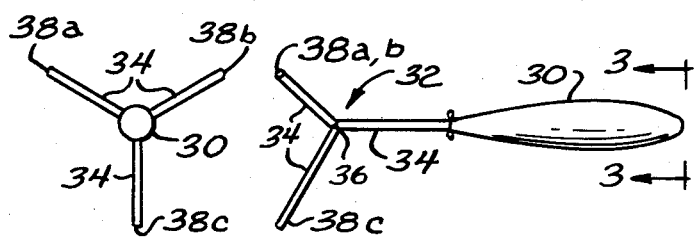
FIG. 2 is a side elevation view of the cursor of the present invention.
FIG. 3 is a front elevation view of the same cursor taken along line 3—3 of FIG. 2.

Cursor 12, illustrated in FIGS. 2 and 3, includes a handle member 30 extending outwardly along one leg of a line attachment member 32. Attachment member 32 is comprised of four equally spaced legs 34 rigidly affixed to a center hub 36 thereby forming a regular tetrahedral geometry defined by line attachment vertices 38. As will be described in more detail below, three separate control lines are attached to each of the four vertices 38, comprising twelve control lines in total.

Figures 4, 5:
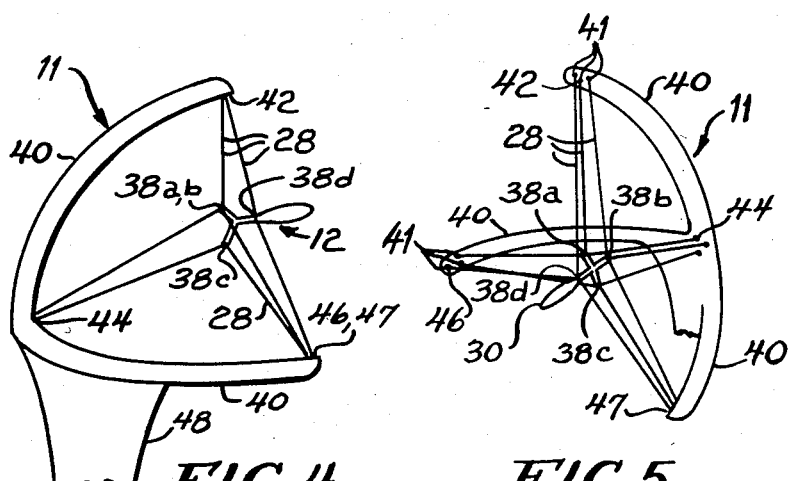
FIG. 4 is a side elevation view of the cursor control unit including the cursor and cursor support structure.
FIG. 5 is a perspective view of the control unit of FIG. 4.

The cursor of the present controller may be suspended, generally, in a icosahedral structure preferably with the twelve control lines spaced equally about a subtending sphere. A regular icosahedral figure is a regular polyhedron having twelve vertices. However, for reasons pertaining to ease of construction and cursor access, an irregular polyhedral arrangement is recommended wherein the lines are brought to a plurality of independent vertices. FIGS. 4 and 5 illustrate a preferred cursor support structure 11 defined by a tetrahedral form wherein three control lines eminate generally from each of four vertices. The cursor support structure 11, shown, is comprised of three contoured arms designed to enhance esthetic appeal while simultaneously minimizing user contact and interference therewith during use. The four vertices are defined as follows: an upper vertex 42, a rear vertex 44, a left front vertex 46, and a right front vertex 47.

Interconnection and routing of the twelve control lines 28 is best shown in FIGS. 4 and 5. Each of the lines 28 is routed from the appropriate cursor vertex 38, through an openings 41 provided in the cursor support structure at respective vertices 42, 44, 46, and 47, through the respective arm members 40, then downwardly through pedestal 48 to the torque motors 24 therebelow. Specifically, the three lines from upper support structure vertex 42 attach to cursor vertices 38$a,b,d$; the lines from rear support vertex 44 interconnect with cursor vertices 38$a,b,c$; the three lines eminating from the left front vertex 46 attach to cursor vertices 38$a,c,d$; and the lines from the right front support vertex 47 connect to cursor vertices 38$b,c,d$. In this manner cursor 12 is supported generally in the center of the support structure 11 by the twelve control lines 28 which, significantly, are each maintained under tension by respective torque motors 24. As the cursor is variously repositioned within its working region, approximately defined by the area between the support structure vertices, the torque motors continuously adjust the lengths of lines 28, as described in more detail below, to assure a predetermined line tension irrespective of the position of the cursor or the fact that the cursor is being moved closer to a given support structure vertex. Thus, a positive tension force is present on each control line during normal operation of the present controller.

The precise position and orientation of the cursor is uniquely determined by the lengths of the twelve lines 28 between the respective cursor and support structure vertices. Any convenient means for measuring these line lengths may be provided, for example, a shaft encoder on the torque motor line spindles. The line length data is fed to computer 16 which performs the necessary calculations. More particularly, the precise location of any given cursor vertex 38$a,b,c,d$ is determined by a mathematical triangulation technique based on the lengths of the three control lines interconnecting the cursor vertex with the support structure. It will be appreciated that the overall position and orientation of the cursor is fixed once the location of the four cursor vertices 38 is known. The position of each of each cursor vertex may be determined utilizing the same mathematical relationships, but appropriately referenced to the proper three support structure vertices.

Figure 6:
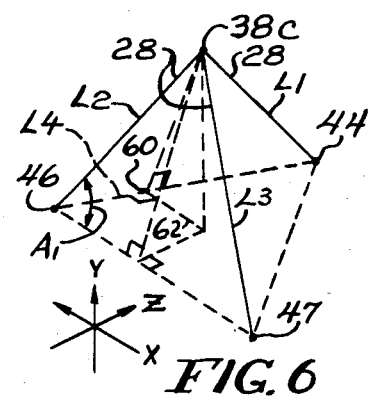
FIG. 6 is a geometric diagram in perspective illustrating the relationship between a cursor line attachment vertex and the corresponding support structure vertices.
Figure 7:
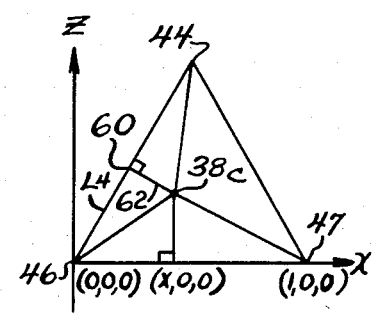
FIG. 7 is a geometric diagram taken from the top of FIG. 6 looking downwardly along the y-axis further illustrating the interrelationships between cursor and cursor support structure vertices.

FIGS. 6 and 7 illustrate the mathematical triangulation technique utilized to locate a cursor vertex. Specifically, FIGS. 6 and 7 show cursor vertex 38$c$ in relation to support structure vertices 44, 46, and 47 through which three control lines 28 interconnect cursor vertex 38$c$ with corresponding torque motors. The distances between the various supporting structure vertices 44, 46, and 47 are, of course, fixed by that structure and known. For the purposes of this illustration, it is assumed that the distances between each pair of vertices 44, 46, and 47 is one unit.

The angle A1 is determined by applying the well known 'law of cosines' relationship as follows:

$$\cos (A1) = ((L2)^2 + 1 - (L3)^2/2 \cdot L2)$$

With the angle A1, the X-coordinate of 38$c$ is defned by:

$$X_c = L2 \cos (A1)$$

As previously discussed, the lengths of lines 28 from cursor vertex 38$c$ to the lower support structure vertices 44, 46 and 47 are also known and are designated respectively as L1, L2, and L3. A conventional orthogonal axes system has been defined with the origin positioned at vertex 46 and with vertex 47 located on the X axis at the point (1,0,0). The XZ plane is defined by the three support structure vertices 44, 46, and 47. There are, of course, several appropriate alternative mathematical solutions to locating cursor vertex 38$c$ in the XYZ coordinate system. For illustration, it is assumed that computer 16 has been programmed to perform the following steps to ascertain the location of vertex 38$c$. However, the present invention contemplates any derivation which properly locates the vertices in question.

The law of cosines is again applied in the manner just described to obtain L4, the length of the line between vertex 46 and point 60. The ratio of L4/1 (1 being the arbitrarily chosen distance between vertices 44, 46 and 47) is multiplied by the coordinates of vertex 44 to establish the coordinates of point 60:

$$L4 (0.5, 0, 0.866) = (0.5[L4], 0, 0.866[L4])$$

Next, the equation of line 62 is derived by the conventional algebraic point-slope technique knowing the coordinates of point 60 and the slope of line 62. The equation of line 62 is given by:

$$(Z - Z_1) = m(X - X_1)$$

where X1 and Z1 are given by point 60 as [0.5(L4), 0.866(L4)] and "m" is defined as:

$$m = -1/\text{Slope of L4} = -0.5/0.866 = -0.577$$

Next, the Z coordinate of vertex 38$c$ may be calculated by solving for the intersection of line 62 and the line $x = X_c$, where $X_c$ is the X coordinate of vertex 38$c$ previously calculated. Finally, the Y coordinate of vertex 38$c$ may be obtained by:

$$Y_c^2 = h^2 - Z_c^2$$

where $h = L2 \sin (A1)$ and $Z_c$ is the Z coordinate of vertex 38$c$ previously derived.

It is again noted that the above method of calculating the precise location of cursor vertices from known line lengths in relation to a known support structure geometry merely illustrates one, of many, mathematical approaches to achieve the same result. The mathematical relationships necessary to properly program computer 16 are well known, even for more complex non-symmetrical supporting structures and, therefore, will not be considered in more detail herein.

As previously described, the twelve control lines are interconnected with torque motors 24 which, in turn, are variably 'programmed' by the control computer 16 to apply a given tension to each of the lines. Thus, as the cursor is moved within its supporting structure, the torque motors 'reel-in' excess or slack line and 'play-out' additional line as required to maintain the programmed line tension. The individual line tensions are programmed by the computer in accordance with the forces actually encountered by the slaved apparatus during use. Specifically, a set of piezoelectric or similar force transducers 50 are mounted on the slaved apparatus and generate the force signals necessary for computer processing. In this manner, cursor force feedback is provided which permits the user to "feel" the tool forces substantially the same as if the procedure were being performed directly with the tool or slaved apparatus in hand. The relative cursor-tool forces and/or movement can be scaled as appropriate for the procedure being performed. Thus, a given movement of the cursor may be scaled upwardly to produce increased motion of the slaved tool or, importantly, the movement of the cursor may be scaled downwardly to provide for the precise motional control of, for example, delicate surgical instruments or the like. Similarly, the respective line tensions programmed by the computer may be scaled to provide the user with either an enhanced or attenuated force feedback response. Thus, a critical surgical procedure requiring extremely precise and 'light' tool pressures can be scaled to provide the surgeon with an increased and meaningful cursor force response.

In addition, the individual line tensions must be continuously updated by the computer to reflect changes in the position of the cursor within the support structure since the resultant force acting upon the cursor, for any given set of individual line tensions, is a function of the particular position of the cursor. This dependency relationship is due to the fact that the relative angles between the cursor legs and the support structure vertices vary according to the position of the cursor within the support structure which results in a changing set of force vectors acting upon the cursor legs by the respective tension lines. Thus, where a constant cursor force is desired, for example, when the slaved apparatus is freely moving within a workspace without encountering an object or workpiece, the computer must repeatedly recalculate the individual line tensions as necessary to maintain this constant overall cursor tension. In addition, it will be appreciated that changes in overall cursor force due to corresponding changes in the resistance to movement of the slaved apparatus, must similarly be adjusted by the computer to account for the actual position of the cursor within its supporting structure. A set of mathematical equations defining the relationships between line tensions, cursor position, and resulting cursor forces can be derived using conventional algebraic and geometric principles in a manner similar to that outlined above. Computer 16 solves these equations in accordance with the known cursor position and slaved apparatus force data thereafter outputting the necessary control signals to torque motors 24.

The twelve tension line cursor support structure described herein facilitates a wide range of cursor motions along the lineal as well as torsional axes maintaining, at all times, a positive tension force on each of the control lines and a corresponding positive or unidirectional force output from each of the tension inducing torque motors 24. Thus, the present arrangement completely avoids regions of difficult or unstable operation characterized by near zero or reversing cursor actuation forces. It should be noted that the present controller is not limited to tetrahedral line attachment and cursor support structures such as shown herein, but may include a variety of other tension line geometries including, for example, a three axes orthogonal structure wherein each of the attachment legs is oriented at 90 degrees with respect to the adjacent legs. However, the disclosed tetrahedral solution is preferred as offering significant advantages relating to overall user accessibility of the cursor and, importantly, in the simplicity of the mathematical solution to the vertex position equations. Unlike the equations outlined above for locating each of the four cursor vertices of the tetrahedral arrangement, the mathematical relationships of the orthogonal cursor and supporting structure require the solution of complex simultaneous equations. This is due to the fact that the orthogonal cursor contains six vertices, each with two lines connected thereto, the position of which can not be uniquely determined without reference to line lengths interconnecting other cursor vertices. In any event, the general twelve vertex, octahedral structure exhibits the highly beneficial property of full multi-axes control with a unidirectional actuating force on each interconnecting actuation member as previously discussed.

It will be understood that changes may be made in the details of construction, arrangement and operation without departing from the spirit of the invention especially as defined in the following claims.

What is claimed is:

1. A controller for remotely manipulating objects including:
   (a) a cursor having a line attachment member for retaining control lines in spaced relationship and a handle means connected thereto for repositioning the attachment member;
   (b) a cursor support means surrounding the cursor having a plurality of means adapted to receive control lines for movement therethrough;
   (c) a plurality of control lines each connected at a first end to the line attachment member and at a second end adapted for connection to a controlled apparatus, the cursor and attachment member being suspended within the cursor support means by said plurality of control lines, each line directed through the receiving means of the support means wherein movement of the cursor handle means correspondingly actuates the controlled apparatus.

2. The controller of claim 1 wherein the line attachment member includes a plurality of spaced leg members rigidly interconnected at, and oriented outwardly from, a common center hub means.

3. The controller of claim 2 wherein the line attachment member includes four leg members equally spaced about the hub means, the ends of the leg members defining a regular tetrahedron whereby a plurality of control lines are attached to each leg member end.

4. The controller of claim 2 wherein the handle means is rigidly connected to, and defines the outward extension of, a leg member.

5. The controller of claim 1 including twelve control lines thereby facilitating full cursor control movement with respect to three independent lineal and three independent torsional axes.

6. The controller of claim 5 wherein the line receiving means of the support means are arranged into four groups, each group comprising three line receiving means; the groups being positioned on the support means to define a volume therebetween wherein the cursor means is suspended.

7. A controller for remotely manipulating objects including:
   (a) a cursor having a line attachment member for retaining control lines in spaced relationship and a handle means connected thereto for repositioning the attachment member;

(b) a cursor support means surrounding the cursor having a plurality of means adapted to receive control lines for axial movement therethrough;

(c) a plurality of control lines each connected at a first end to the line support member and at a second end to motor tensioning means, each line directed through the line receiving means of the support means wherein the motor tensioning means is adapted to reel-in or play-out control lines as the cursor is manipulated within the support means.

8. The controller of claim 7 including means for generating signals representative of the lengths of the control lines between the line attachment member and tensioning means.

9. A controller for remotely manipulating objects including:

(a) a cursor including a line attachment member and a handle means connected thereto, the line attachment member having four vertices defining a tetrahedral geometry; means on each vertex for attaching three support lines thereto;

(b) cursor support means surrounding the cursor including four corners defining a volume therebetween wherein the cursor is suspended for manipulation;

(c) means associated with each support means corner adapted to receive three control lines for movement therethrough;

(d) twelve control lines each having a first end connected to a vertex of the line attachment member and a second end adapted for connection to a controlled apparatus, three of said control lines being directed through the line receiving means of each support means corner whereby movement of the cursor handle means causes a corresponding response in said controlled means.

10. The controller of claim 9 wherein the three control lines from the first support means corner connects to the first, second, and third vertices of the attachment member; the three control lines from the second support means corner connect to the first, second, and fourth attachment member vertices; the three control lines from the third support means corner connect to the first, third, and fourth attachment member vertices; and the three control lines from the fourth support means corner connect to the second, third, and fourth vertices of the attachment member.

* * * * *